United States Patent
Jackson et al.

(10) Patent No.: US 7,714,301 B2
(45) Date of Patent: *May 11, 2010

(54) INSTRUMENT EXCITATION SOURCE AND CALIBRATION METHOD

(75) Inventors: Joseph H. Jackson, El Granada, CA (US); Robert M. Gavin, III, Cupertino, CA (US); Richard C. Tighe, Half Moon Bay, CA (US); Steve McNerney, San Jose, CA (US); Wu Jiang, Sunnyvale, CA (US); Todd E. French, Sunnyvale, CA (US); Reginald Tobias, Ware, MA (US)

(73) Assignee: Molecular Devices, Inc., Sunnyvale, CA (US)

( * ) Notice: Subject to any disclaimer, the term of this patent is extended or adjusted under 35 U.S.C. 154(b) by 343 days.

This patent is subject to a terminal disclaimer.

(21) Appl. No.: 11/100,320

(22) Filed: Apr. 5, 2005

(65) Prior Publication Data

US 2005/0285129 A1 Dec. 29, 2005

Related U.S. Application Data

(63) Continuation-in-part of application No. 10/003,030, filed on Oct. 29, 2001, now Pat. No. 6,930,314.

(60) Provisional application No. 60/244,012, filed on Oct. 27, 2000.

(51) Int. Cl.
*G01N 21/64* (2006.01)
(52) U.S. Cl. ............... 250/458.1; 250/459.1; 250/461.2
(58) Field of Classification Search ............ 250/458.1, 250/461.2; 356/311, 246, 417, 244
See application file for complete search history.

(56) References Cited

U.S. PATENT DOCUMENTS

| 3,431,437 | A | * | 3/1969 | Kosonocky ............... 372/8 |
| 3,837,746 | A | * | 9/1974 | Acker et al. ............ 356/440 |
| 3,906,239 | A | * | 9/1975 | Smith et al. .......... 250/559.17 |
| 3,975,098 | A | | 8/1976 | West |
| 4,460,274 | A | | 7/1984 | Schumann et al. |
| 4,478,094 | A | | 10/1984 | Salomaa et al. |
| 4,501,970 | A | | 2/1985 | Nelson |
| 4,537,861 | A | | 8/1985 | Elings et al. |
| 4,626,684 | A | | 12/1986 | Landa |
| RE32,598 | E | | 2/1988 | White |
| 4,764,342 | A | | 8/1988 | Kelln et al. |

(Continued)

FOREIGN PATENT DOCUMENTS

EP  0 410 645 A2  1/1991

(Continued)

*Primary Examiner*—David P Porta
*Assistant Examiner*—Casey Bryant
(74) *Attorney, Agent, or Firm*—Morgan, Lewis & Bockius LLP

(57) ABSTRACT

An apparatus including an LED excitation source and module useful for full plate imaging fluorescence instruments as well as methods for calibrating such instruments. The apparatus may include a light source operative to provide simultaneous illumination of a first wavelength selected to a plurality of samples to excite the fluorescent emission of light of a second wavelength by said plurality of samples wherein the light source is an LED array; and an optical sensor, responsive to light at said second wavelength.

27 Claims, 7 Drawing Sheets

U.S. PATENT DOCUMENTS

| | | | |
|---|---|---|---|
| 4,818,710 A * | 4/1989 | Sutherland et al. | 436/527 |
| 4,935,665 A * | 6/1990 | Murata | 313/500 |
| 5,100,238 A * | 3/1992 | Nailor et al. | 356/246 |
| 5,325,295 A | 6/1994 | Fratantoni et al. | |
| 5,355,215 A | 10/1994 | Schroeder et al. | |
| 5,443,791 A | 8/1995 | Cathcart et al. | |
| 5,460,943 A | 10/1995 | Hayashi et al. | |
| 5,477,332 A | 12/1995 | Stone et al. | |
| 5,591,981 A | 1/1997 | Heffelfinger et al. | |
| 5,670,113 A | 9/1997 | Akong et al. | |
| 5,784,152 A | 7/1998 | Heffelfinger et al. | |
| 5,828,452 A | 10/1998 | Gillispie et al. | |
| 5,938,617 A | 8/1999 | Vo-Dinh | |
| 5,948,673 A | 9/1999 | Cottingham | |
| 5,959,738 A | 9/1999 | Hafeman et al. | |
| 5,973,842 A | 10/1999 | Spangenberg | |
| 5,978,095 A | 11/1999 | Tanaami | |
| 6,011,626 A | 1/2000 | Hielscher et al. | |
| 6,022,141 A | 2/2000 | Bass | |
| 6,024,920 A | 2/2000 | Cunanan | |
| 6,043,880 A * | 3/2000 | Andrews et al. | 356/311 |
| 6,057,114 A | 5/2000 | Akong et al. | |
| 6,069,011 A | 5/2000 | Riedel | |
| 6,075,592 A * | 6/2000 | Banerjee et al. | 356/318 |
| 6,097,025 A | 8/2000 | Modlin et al. | |
| 6,127,133 A | 10/2000 | Akong et al. | |
| 6,372,183 B1 | 4/2002 | Akong et al. | |
| 6,759,662 B1 * | 7/2004 | Li | 250/458.1 |
| 6,813,017 B1 * | 11/2004 | Hoffman et al. | 356/317 |
| 6,825,927 B2 * | 11/2004 | Goldman et al. | 356/317 |
| 6,852,986 B1 * | 2/2005 | Lee et al. | 250/458.1 |
| 6,930,314 B2 * | 8/2005 | Jackson et al. | 250/458.1 |
| 2001/0048899 A1 | 12/2001 | Marouiss et al. | |
| 2002/0109100 A1 | 8/2002 | Jackson et al. | |
| 2002/0176801 A1 | 11/2002 | Giebeler et al. | |
| 2003/0230728 A1 * | 12/2003 | Dai et al. | 250/458.1 |
| 2004/0033554 A1 | 2/2004 | Powers | |
| 2004/0149998 A1 * | 8/2004 | Henson et al. | 257/98 |

FOREIGN PATENT DOCUMENTS

| | | |
|---|---|---|
| EP | 0 410 645 A3 | 1/1991 |
| JP | 359126392 A * | 7/1984 |
| WO | WO 97/11351 A1 | 3/1997 |
| WO | WO 97/11352 A1 | 3/1997 |
| WO | WO 00/06990 A2 | 2/2000 |
| WO | WO 00/06990 A3 | 2/2000 |
| WO | WO 00/06991 A2 | 2/2000 |
| WO | WO 00/06991 A3 | 2/2000 |
| WO | WO 00/50877 A1 | 8/2000 |
| WO | WO 00/66269 A1 | 11/2000 |
| WO | WO 01/04608 A1 | 1/2001 |

* cited by examiner

INSTRUMENT EXCITATION SOURCE AND CALIBRATION METHOD

CROSS-REFERENCES TO RELATED APPLICATIONS

This application claims priority to U.S. Provisional Patent Application No. 60/559,634, filed Apr. 5, 2004 and entitled INSTRUMENT EXCITATION SOURCE AND CALIBRATION METHOD, the entire contents of which is incorporated herein by this reference.

This application is a Continuation-in-Part of U.S. patent application Ser. No. 10/003,030 filed Oct. 29, 2001 now U.S. Pat. No. 6,930,314 and entitled LIGHT DETECTION DEVICE, which claims priority to U.S. Provisional Patent Application No. 60/244,012 filed Oct. 27, 2000 and entitled LIGHT DETECTION DEVICE, the entire contents of which is incorporated herein by reference.

BACKGROUND OF THE INVENTION

1. Field of the Invention

This invention concerns an LED excitation source and module useful for full plate imaging fluorescence instruments as well as methods for calibrating such instruments.

2. Description of Related Art

Spectroscopy involves the study of matter using electromagnetic radiation. Spectroscopic measurements can be separated into three broad categories: absorbance, scattering/reflectance, and emission. Absorbance assays involve relating to the amount of incident light that is absorbed by a sample to the type and number of molecules in the sample. Absorbance assays are a powerful method for determining the presence and concentration of an analyte in a sample. Most commonly, absorbance is measured indirectly by studying the portion of incident light that emerges from the sample. Scattering assays are similar to absorbance in that the measurement is based on the amount of incident light that emerges or is transmitted from the sample. However, in the case of scattering, the signal increases with the number of interactions, whereas, in the case of absorbance, the signal is inversely proportional to the interactions. Emission assays look at electromagnetic emissions from a sample other than the incident light. In each case, the measurements may be broad spectrum or frequency specific depending on the particular assay. Most commonly, emission assays involve the measurement of luminescence. The techniques of absorbance, scattering/reflectance, and luminescence are described in detail in the following patent applications, which are hereby incorporated by reference in their entirety for all purposes: WIPO Publication No. WO 00/06991, published Feb. 10, 2000; and corresponding U.S. patent application Ser. No. 09/765,869, filed Jan. 19, 2001.

Luminescence is a preferred assay technique due to its specificity and sensitivity, among others. Luminescence is the emission of light from excited electronic states of atoms or molecules. Luminescence generally refers to all kinds of light emission, except incandescence, and may include photoluminescence, chemiluminescence, and electrochemiluminescence, among others. In photoluminescence, which includes fluorescence and phosphorescence, the excited electronic state is created by the absorption of electromagnetic radiation. In chemiluminescence, which includes bioluminescence, the excited electronic state is created by a transfer of chemical energy. In electrochemiluminescence, the excited electronic state is created by an electrochemical process.

Luminescence assays are assays that use luminescence emissions from luminescent analytes to study the properties and environment of the analyte, as well as binding reactions and enzymatic activities involving the analyte, among others. In these assays, the analyte itself may be the focus of the assay, or the analyte may simply act as a reporter that provides information about another material or target substance that is the true focus of the assay. Recently, luminescence assays have been used in high throughput procedures to screen pharmaceutical drug candidate libraries for drug activity and to identify single-nucleotide polymorphisms (SNPs).

Luminescence assays may involve detection and interpretation of one or more properties of the luminescence or associated luminescence process. These properties may include intensity, excitation and/or emission spectrum, polarization, lifetime, and energy transfer, among others. These properties also may include time-independent (steady-state) and/or time-dependent (time-resolved) properties of the luminescence. Representative luminescence assays include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and bioluminescence resonance energy transfer (BRET), among others.

Luminescence assays have been conducted using various light sources, including arc lamps and lasers. Unfortunately, these light sources suffer from a number of shortcomings. The gas used in arc lamps typically is under high pressure, so that explosion is always a danger, and the associated power supplies may produce transients that can damage other electronic components of the system. The lifetime of arc lamps may be short, so that the lamps must be changed frequently. Moreover, typical arc lamps (including flash arc lamps) suffer from intensity instability, with short term noise of several percent, which is much worse than good lasers such as laser diodes and diode pumped solid-state lasers, with short-term noise of typically less than 0.5%. In addition, lamps have a slow and steady long-term decay of intensity, whereas lasers normally exhibit a constant intensity up until catastrophic failure. The spectral output of some arc lamps and most lasers is very limited, so that desired excitation wavelengths may not be available. For example, two commonly used light sources, the mercury arc lamp and the argon-ion laser, produce significant visible light only at two wavelengths below about 550 nm. Moreover, the procedure for switching or tuning between these wavelengths can be so cumbersome and impractical that some experimentalists have resorted to the expensive alternative of incorporating multiple lasers into their instrumental setups. Significantly, an ability to use and switch between various excitation wavelengths would permit use of a wider variety of dyes, which in turn would facilitate the development of new luminescence assays, including new high throughput cell-based luminescence assays.

Luminescence assays also have been conducted using various detection schemes. These schemes may require alignment of a sample and portions of an optical relay structure (such as an optics head) for directing light to and from the sample. This alignment typically is accomplished by physically moving the sample relative to the optical relay structure and/or by physically moving the optical relay structure relative to the sample. This movement may be followed by a waiting period before measurement to allow vibrations to subside. Time spent during alignment and subsequent waiting periods is downtime because it is time during which data cannot be collected from the sample. This downtime is especially significant in high-throughput screening, where tens or hundreds of thousands of samples must be aligned with an optical relay structure to conduct a particular study.

In principle, reading simultaneously from a plurality of samples or from a larger area of a single sample can reduce the number of alignment steps and thus the amount of downtime in these assays. Indeed, instrumentation has been developed that directs light from an arc lamp or from a continuous wave laser tuned to a single fixed wave length to multiple wells of a microplate using a mechanical (e.g., rotating polygon or galvanometric) scanner and/or a wide-field illuminator. However, reading with the scanner is slow, because samples are analyzed well by well, and reading with the widefield imager reduces intensities, because excitation light is distributed to areas between or outside the samples. Reduced intensities may decrease signal-to-noise ratios, decreasing reliability, especially with less intense nonlaser light sources. Prior art instrument systems also may be limited because it may be difficult to change the emission filter to correspond to a change in excitation wavelength. This is especially true with simultaneous reading because filters for simultaneous reading may need to be quite large to filter emission light passing from large-area samples, such as microplates, to large-area imaging devices, such as charge-coupled devices (CCDs), charge injection device (CID) arrays, videcon tubes, photomultiplier tube arrays, position sensitive photomultiplier tubes, and the like. Significantly, it is desirable to increase the number of measurements made in a given time period. Increased data collection rates together with faster analysis would give more specific and quantitative information regarding the speed and strength of cellular responses to potential drug candidates.

Typical fluorescence imaging microplate readers use lamps and continuous wave argon-ion laser as excitation sources. In laser excitation systems, the intense collimated energy of the beam is expanded via a concave mirror and piano-convex cylindrical lens and rastered across the microplate hundreds of times per second with a faceted rotating drum scanner. Prior art fluorescence imaging instruments that use a laser excitation source are disclosed, for example in U.S. Pat. No. 5,355,215, in published U.S. Patent Application Publication No. US 2003/0223910 A1, in U.S. Patent Application Publication No. US 2002/0109100 A1, and in U.S. patent application Ser. No. 10/738,438, the entire contents of which are incorporated herein by this reference.

An advantage of the laser system is high energy output and very narrowband excitation. Disadvantages of the laser systems include (1) its large size (over 5' long), (2) great weight; (3) its complexity (required several hours set-up and alignment by a skilled technician); (4) its cost (~$25,000); (5) significant ongoing service requirements and infrastructure requirements (cooling water and 208V); and (5) limited wavelength range (typically 488 nm and 514 nm for an argon ion laser).

BRIEF SUMMARY OF THE INVENTION

One aspect of this invention is an LED array comprising at least two LEDs; a reflector surrounding each LED and having an opening; and a tubular section adjacent to each reflector opening. In an optional aspect, the LED array may include at least two LED's arranged in a linear array. In another optional aspect, the LED array may include at least two of the LED's emit energy at different wavelengths. In yet another optional aspect, the LED array tubular section may have an inner surface at least a portion of which has low reflectivity. In still another optional aspect, the LED array inner surface portion may be black.

Another aspect of this invention is an LED module comprising: a plurality of LEDs arranged in a linear array; a reflector surrounding each LED and having an opening; and a tubular section adjacent to each reflector opening. In an optional aspect, the LED module tubular section may include an inlet aperture and an outlet aperture and wherein a filter covers the outlet aperture. In another optional aspect, the LED module may include a heat sink associated with at least one of the plurality of LEDs.

Another aspect of this invention is an LED bank comprising at least two LED modules each comprising: a plurality of LEDs arranged in a linear array; a reflector surrounding each LED and having an opening; and a tubular section adjacent to each reflector opening, wherein the LED arrays are associated with each other such that the linear array of LEDs are parallel to each other and face in the same direction. In an optional aspect, all of the LEDs of a first LED module emit light with essentially the same spectra and wherein all of the LEDs of a second LED module emit light with essentially the same spectra wherein the LEDs of the first module do not emit light with essentially the same spectra of the light emitted from the LEDs of the second LED module.

Still another aspect of this invention is an apparatus for the measurement of a fluorescent emission from at least one sample, each sample being supported adjacent or embedded within a medium capable of contributing to background fluorescence, said apparatus comprising: (1) a light source operative to provide illumination of a first wavelength selected to excite the fluorescent emission of light of a second wavelength by said samples wherein the light source is an LED array; and (2) an optical sensor, responsive to light at said second wavelength. In an optional aspect, the light source is an LED module comprising a plurality of LEDs arranged in a linear array, a reflector surrounding each LED and having an opening, and a tubular section adjacent to each reflector opening. In another optional aspect, the light source is at least one LED bank comprising at least two LED arrays wherein the LED arrays are associated with each other such that the linear array of LEDs are parallel to each other and face in the same direction. In still another optional aspect, the light source is a pair of opposing LED banks and optionally LED banks that are oriented such that the energy emitted from the LEDs is angled at the bottom of the at least one sample at an oblique angle relative to the optical window of the at least one sample) holder. Optionally the oblique angle is an angle of about 45 degrees. In another optional aspect, a non-imaging optic is located between the LED bank and the at least one sample wherein the non-imaging optic is optionally a reflective light pipe. In another optional aspect, the apparatus includes at least one photodiode that optically samples the output of the LED array wherein the at least one photodiode is optionally located at a position selected from between the LED array and the at least one sample and remote from the LED array or a combination of both locations.

Still another aspect of this invention includes a method for measuring a fluorescent emission from at least one sample located in a well, each sample being disposed adjacent a background fluorescence producing medium, said method including the steps of: (1) providing at least one LED light source which emits illumination of a first wavelength selected to excite the fluorescent emission of light of a second wavelength by said samples; (2) activating the light source to project illumination of said first wavelength onto said at least one sample, so as to excite the fluorescent emission of light of said second wavelength there from; (3) disposing an optical sensor, responsive to illumination of said second wavelength, so as to receive light emitted from the at least one sample; (4) sensing the intensity of light emitted from the at least one sample with said optical sensor and converting the intensity sensed into a intensity value; and (5) correcting the intensity value by a correction factor method selected from the group consisting of source normalization, flat fielding, background subtraction, and luminescent assay correction to obtain a corrected intensity value. In an optional aspect, the intensity value is corrected by using at least two of the correction methods.

In the method above, the intensity value may be corrected by flat fielding by the further steps of: (i) determining the electronic offset for a fluorescent plate; (ii) taking a fluorescence image of a uniformly fluorescent plate with a camera having a plurality of pixels to form a first multi-pixel image; (iii) subtracting pixel by pixel the electronic offset from the first multi-pixel image; (iv) reversing the plate and taking a second multi-pixel image; (v) subtracting pixel by pixel the electronic offset from of the second multi-pixel image; (vi) adding pixel by pixel the resultant of the first multi-pixel image and the second multi-pixel image; (vii) dividing the result of step (vi) by 2 and storing the result as a 2-image average; (viii) defining the regions of the image comprising the individual wells of the assay plate and calculate the average pixel intensity for each well; (ix) identifying the highest intensity value well, and dividing this number by each of the other well intensity averages to form a matrix of values (one for each well) to give a spatial correction factor for each well wherein the highest value well will have a correction factor of 1.0 and all the other well correction factors will be higher than 1; and (x) storing this matrix as the Fluorescence Spatial Correction Factor XXX, where XXX is the wavelength of the excitation bank used and wherein each bank of LEDs will have its own matrix.

In the method above, the intensity value may be corrected by background subtraction by the further steps of: (i) taking an image of a reference plate when the LED array is activated to form a background template; (ii) calculating a background power factor associated with the background template; (iii) taking a plurality of images of the reference plate, each imaging being taken at essentially identical conditions except for a camera gain setting; (iv) recording the camera output from step (3) and identifying the actual camera gain for each image; (v) calculating the relationship between the camera gain setting and the actual to camera gain; (vi) taking an assay image and identifying the assay image power factor; and (vii) correcting the assay image by multiplying the ratio of the assay image power factor:background power factor and subtracting the result from the assay image.

In the method above, the reference power factor and the assay image power factors are each the product of the average of the two photodiodes and the relative gain.

In the method above, the intensity value may be corrected by luminescent assay correction by the further steps of: (i) taking a first luminescence image of a uniformly luminescent plate; (ii). subtracting an ADC Offset from the image; (iii) reversing the plate and take a second image; (iv) subtracting the ADC Offset from the second image; (v) adding together the resultant first and second images; (vi) dividing the results of step (5) by 2 and storing the result as a luminescence spatial correction factor; (vii) preparing a luminescence image for a sample plate; (viii) subtract ADC Offset from sample plate luminescent image; (ix) applying a mask definition to identify individual wells in the sample plate; and (x) multiplying the resultant image by the appropriate luminescence spatial correction factor.

In the method above, the intensity value may be corrected by source normalization by the further steps of: (i) activating the LED array a first time; (ii) sampling the emitted light with at least one photodiode; (iii) recording the value measured by the at least one photodiode and identifying the value measured as a reference value; (iv) activating the LED array a second time and measuring the emitted light to give an emitted light value; (v) dividing the reference value with the emitted light value and using the result as a scaled up factor. In this method, two photodiodes may optionally be used and the reference value and the emitted light value are determined by adding the output signals from each photo diode and averaging the results by a method selected from mathematical averaging or weighted averaging.

Another aspect this invention is a light detection device, comprising: an LED light source configured to produce light of a first spectra; a converter configured to receive the light of the first spectra and to convert that light into light of a second spectra, where the second spectra is different than the first spectra; a system for directing the light of the second spectra to an examination area; and a detector configured to receive luminescence light from a sample positioned in the examination area. In this embodiment, the LED light source may be pulsed and the pulsed LED light source may be triggered by the detector.

Yet another aspect of this invention is a light detection device, comprising: an LED light source configured to produce light of a first spectra; a converter configured to receive the light of the first spectra and to convert that light into light of a second spectra, where the second spectra is different than the first spectra; a system for directing the light of the second spectra to an examination area; and a detector configured to receive luminescence light from a sample positioned in the examination area further including a fluid delivery system that includes a dispensing device configured to deliver a fluid material to the sample. In this aspect, the detector may optionally be configured to coordinate the reception of luminescence light from the sample with the delivery of the fluid material to the sample. Moreover, in this embodiment, the light may be used to determine a time-dependent property of the sample.

Still another aspect of this invention is a method and apparatus for detecting light transmitted from a sample, comprising: outputting light from an LED light source, the light having a first spectra; selectively converting the light having the first spectra to light having a second spectra, where the second spectra is different than the first spectra; directing the light having the second spectra onto the sample; and measuring light transmitted from the sample induced by the light having the second spectra wherein one or more reagents are added to a plurality of the sample sites and thereafter directing the light having the second spectra onto the sample sites; measuring light transmitted from the sample induced by the light having the second spectra; and correlating the light transmitted from the sample after addition of the reagents with a characteristic of the sample. In an optional aspect, the step of measuring light transmitted from the sample optionally comprises measuring the light from a plurality of sample sites substantially simultaneously. In another optional aspect, the step of measuring light transmitted from the sample comprises measuring the light from more than eight sample sites substantially simultaneously.

Sill another aspect of this invention is a method and apparatus for detecting light transmitted from a sample, comprising: outputting light from a light source, the light having a first spectra; selectively converting the light having the first spectra to light having a second spectra, where the second spectra is different than the first spectra; directing the light having the second spectra onto the sample; and measuring light transmitted from the sample induced by the light having the second wherein the step of illuminating the sample at a spectra selected to photochemically activate one or more sample components.

Yet another aspect of this invention is a method and apparatus for detecting light transmitted from a sample, comprising: outputting light from a light source, the light having a first spectra; selectively converting the light having the first spectra to light having a second spectra, where the second spectra is different than the first spectra; directing the light having the second spectra onto the sample; and measuring light transmitted from the sample induced by the light having the second spectra wherein the step of exposing the sample to an electrical potential selected to stimulate one or more sample components.

Yet another aspect of this invention is a method an apparatus for detecting light transmitted from a sample, comprising: outputting light from a light source, the light having a first spectra; selectively converting the light having the first spectra to light having a second spectra, where the second spectra is different than the first spectra; directing the light having the second spectra onto the sample; and measuring light transmitted from the sample induced by the light having the second spectra where the light transmitted from the sample is used to determine a time-dependent property of the sample. In another optional aspect, the light transmitted from the sample is used to determine an excited state lifetime for a component of the sample. In still another optional aspect, the light transmitted from the sample is used to determine a reaction time for the sample.

Still another aspect of this invention is a method of detecting luminescence from a luminescent sample, comprising: outputting light from an LED light source, the light being capable of inducing luminescence in the sample; selectively converting the light into light having a preselected intensity; directing the light having the preselected intensity onto a sample holder so that the light is incident at least substantially only on sample sites in the sample holder; and measuring luminescence light transmitted from at least one of the sample sites induced by the light having the preselected intensity. In an optional aspect, the method includes the further step of correlating the measured luminescence with a cellular property. In another optional aspect, the luminescence is used to determine a time-dependent property of the sample and optionally to determine an excited state lifetime for a component of the sample or a reaction time for the sample.

Yet another aspect of this invention is a method of detecting light transmitted from a sample, comprising: outputting light from an LED light source, the light having a 30 first spectra; selectively converting the light having the first spectra to light having a second spectra, where the second spectra is different than the first spectra; directing the light having the second spectra onto the sample; and measuring light transmitted from the sample induced by the light having the second spectra further comprising: exposing the sample to a reagent or an environmental condition; incubating the sample for a time sufficient for the reagent or environmental condition to detectably effect the sample; directing the light having the preselected intensity onto the sample holder; measuring the luminescence light transmitted from at least one of the sample sites induced by the light having the preselected intensity; and comparing the luminescence light transmitted from at least one of the sample sites with the luminescence light to transmitted from the same sample site before the step of exposing the sample to the reagent or the environmental condition. In an optional aspect, the luminescence light transmitted from each of the sample sites is compared with the luminescence light transmitted from that sample site before the step of exposing the sample to the reagent or the environmental condition.

The instrument excitation source and calibration method of the present invention has other features and advantages which will be apparent from or are set forth in more detail in the accompanying drawings, which are incorporated in and form a part of this specification, and the following Detailed Description of the Invention, which together serve to explain the principles of the present invention.

DETAILED DESCRIPTION OF THE INVENTION

Figure 1:
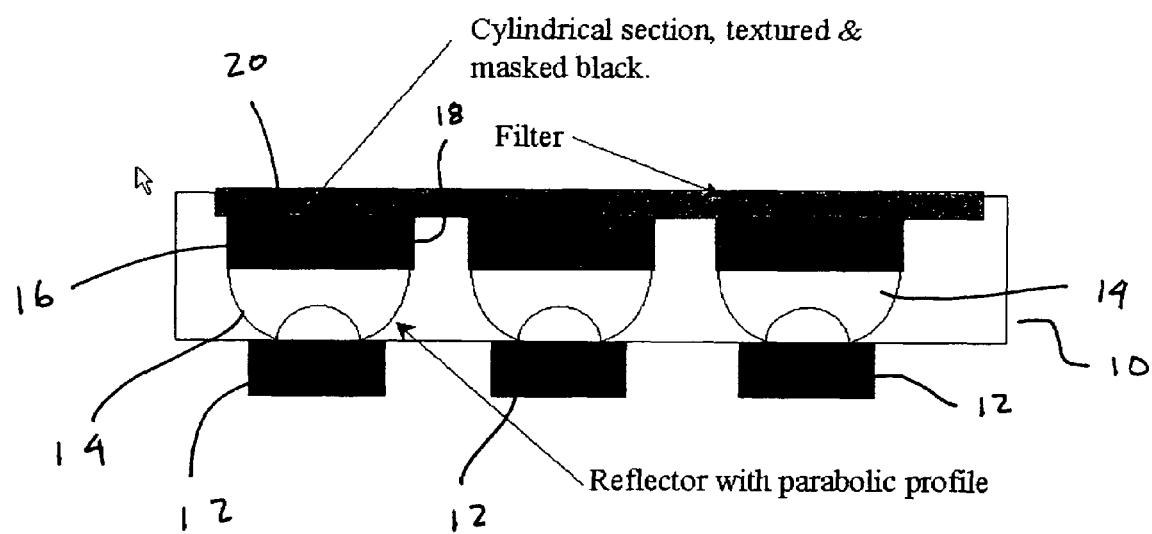
FIG. 1 is a side cut-away view of a portion of one embodiment LED module of this invention.

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

This invention concerns LED excitation sources and modules useful for full plate imaging fluorescence instruments as well as methods for calibrating such instruments.

The apparatuses of this invention take advantage of the naturally wide-angle emission of the LEDs to create relatively uniform excitation of entire microplates with no moving parts. The apparatuses require no alignment by manufacturing, field service, or customers. Customers can easily swap out LED modules to achieve different wavelengths for different assays. There are little to no service requirements. The system components fit in a shoebox, weight less than 10 lbs, require no cooling water and only 24 VDC power, and cost less than $10,000.

The broadband nature of the LED output spectrum generally requires the use of an optical filtering system. Even with optimal filtering, some small amount of residual light from the LEDs in the emission band of the dye can reach the detector creating significant background emission levels. If background emission problems arise, then they can be addressed using one or more of the novel system and/or instrument calibration and data correction methods of this invention.

I. LED Excitation Module

The LED modules of this invention may be used in any instrument that uses an excitation source such as a laser or a light in analytical measurements. The LED modules of this invention are especially useful in fluorescence imaging instruments. An example of a preferred instrument is set forth in U.S. Pat. No. 5,355,215, the entire content of which is incorporated herein by this reference. The '215 instrument provides for the simultaneous measurement of the fluorescent emission from each of a plurality of cellular samples disposed in a multiple well plate. The instrument uses a laser light source which emits illumination of a first wavelength selected to excite the fluorescent emission of light of a second wavelength by the samples. The light source is positioned so as to project illumination of the first wavelength onto a portion of a bottom surface of each of the wells at a first angle of incidence so as to excite the fluorescent emission of light of the second wavelength from the bottom surfaces of the wells. The instrument also includes an optical sensor, responsive to illumination of the second wavelength and positioned above the microwell plate to receive light emitted from the bottom surface of the wells at a second angle such that at least one of the first or second angles is oblique to the bottom surface of the wells. Because of the angular relationship of the source of illumination and detector, the detector does not view a major portion of the reflected excitation light nor the illuminated, fluorescing, supernatant medium. In a preferred embodiment of the present invention, the detector is an imaging detector, e.g., a multi-pixel detector wherein the number of pixels on the detector surface is greater than the number of wells in the micro-well plate. Examples of such detectors include CCD cameras, CID cameras, CMOS cameras, image disectors, and multianode PMTs. Samples, typically biological cells or derivatives, may be held by a variety of vessels including divided culture vessels, microplates, microscope slides, and biochips. The samples may be added to, grown on, reacted to, or assembled on the vessel. The vessel allows optical access to the samples typically via an optical window. However optical access is possible through the open portion of an open sample vessel.

Figure 2:
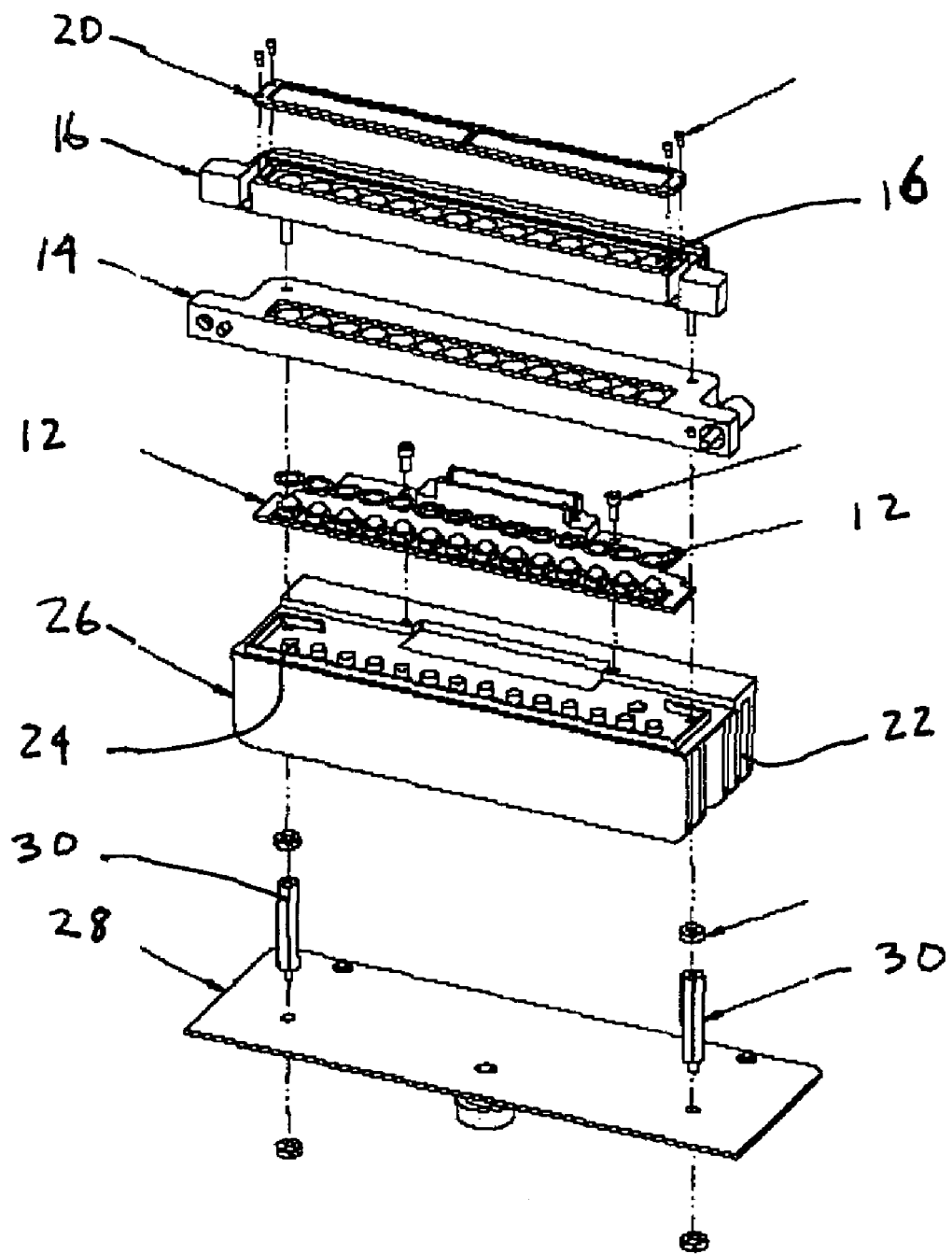
FIG. 2 is an exploded perspective view of one embodiment of an LED module of this invention.
Figure 3:
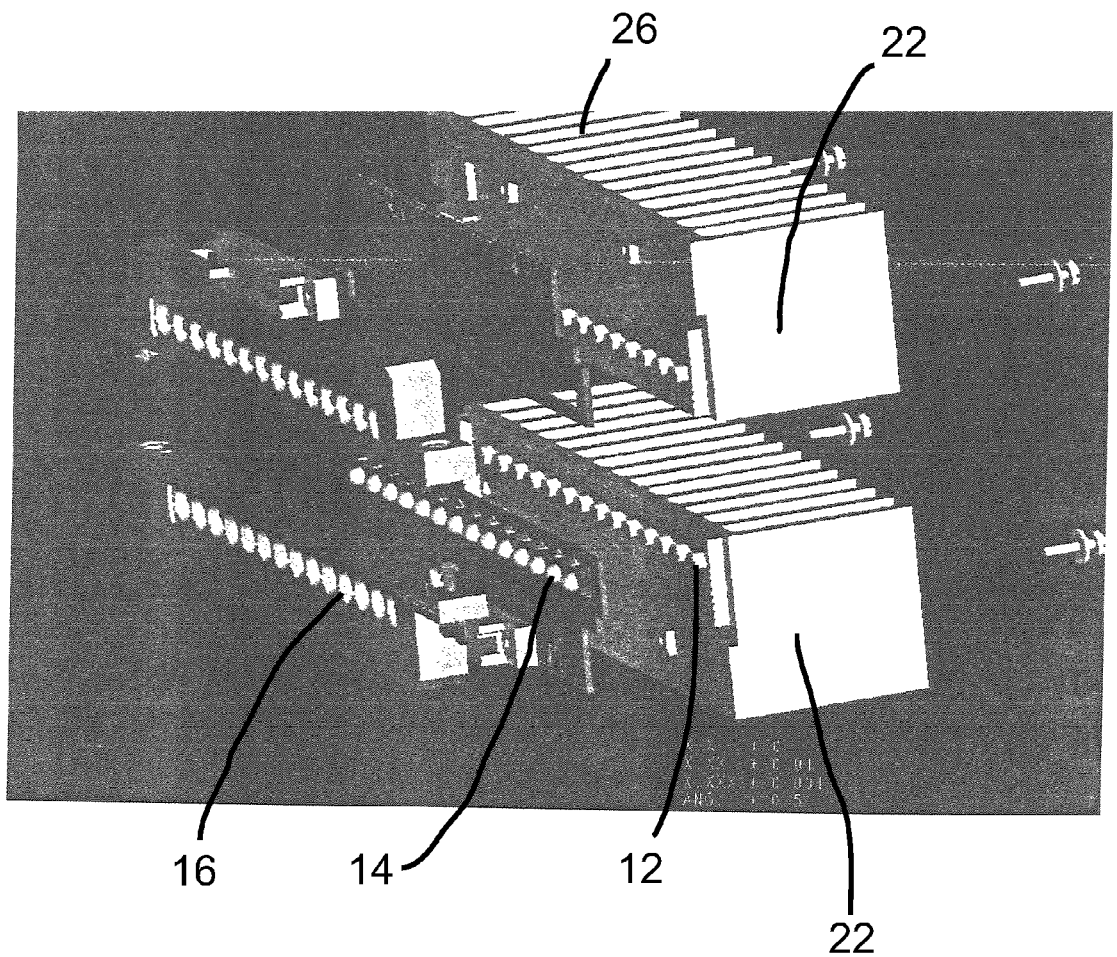
FIG. 3 is an exploded view of an embodiment of an LED assembly of this invention including two LED modules.

One aspect of this invention is an LED module 10 as set forth in FIGS. 1-3. LED module 10 comprises a plurality of LEDs (light emitting diodes) 12 generally arranged in a linear fashion. Commercially available LEDs typically emit blue, green, yellow, red or white light. LEDs typically emit light in a broad spectrum of wavelengths. So there may be some overlap of wavelengths of light emitted by different LED's. As used herein LED's that are "different" refers to LED's that emit different colored light. LED's that are the "same" refers the LEDs that emit light in essentially the same spectra. A plurality of LED's 12 may each emit the same color of light (they may be the same) or they may emit lights of different colors (they may be different). It is preferred that each linear array of LED's emits light of essentially the same spectra. As shown in FIG. 1, each LED 12 includes a reflector 14 around each individual LED 12 to collect and direct the LED energy forward in as collimated fashion as is practical. Reflector 14 is in the shape of a truncated cone. Any shape, however that directs energy forward, such as a conical shape, parabolic shape, ellipsoidal shape, hyperbolic shape, spherical shape, or aspherical shape is suitable. A tubular section 16 immediately adjacent reflector 14 serves to absorb light exiting the LED 10 or reflector 14 at extreme angles. Extreme angles are those that are not close to parallel to the optic axis of the system, e.g., angles greater than 45° from normal. It is preferred that an inner surface portion 18 of tubular section 16 is strongly absorbing, i.e., has a portion of low reflectivity. In a preferred embodiment, the inner surface portion 10 is textured and/or painted or colored with a dark color such as black. Module 10 further includes an optional filter 20 that removes unwanted wavelengths from the LED emitted spectrum.

The elements of LED module 10 describe above are combined with a heat dissipation portion (heat sink with or without fans) 22, as shown in FIGS. 2 and 3. Heat sink 22 includes a plurality of raised portions 24 wherein each raised portion 24 is in thermal contact with an LED 12. The raised portions 24 conduct heat from LEDs 12 into the body of heat sink 22 where it is dissipated by fins 26 and/or by a fan. Heat sink 22 is connected to a plate 28 with one or more connectors 30. One or more LED modules can be associated with each plate 28.

In an alternative embodiment, a collimating lens (either conventional or diffractive) may be placed in front of one or more LEDs 10. The collimating lens collimates the LED emitted light, thereby redirecting rays that would otherwise need to be eliminated by the absorbing section.

Figure 4:
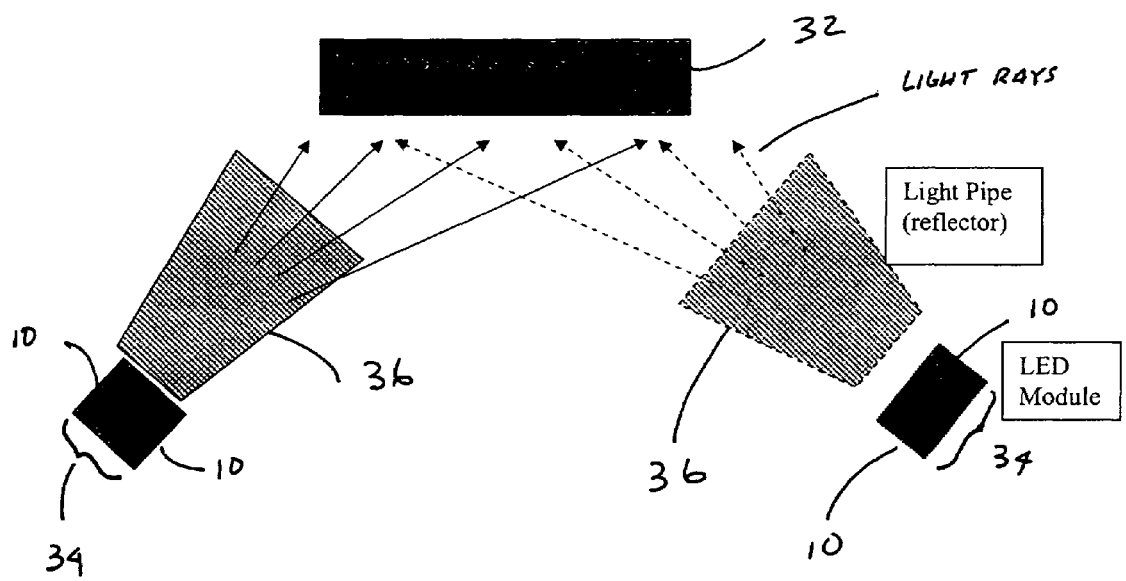
FIG. 4 is a schematic view of an embodiment for orienting a plurality of LED modules of this invention with respect to a microplate.
Figure 5:
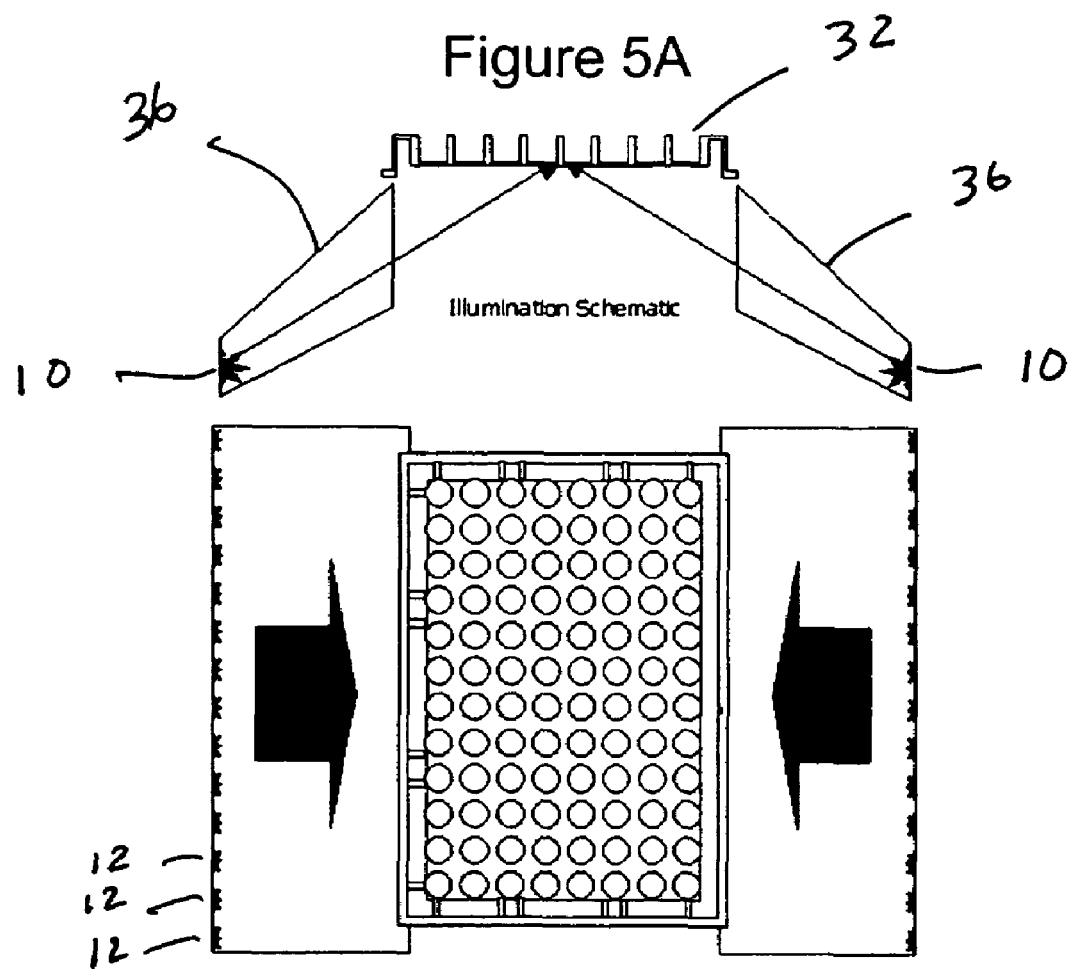
FIGS. 5A and 5B are side and top views of an embodiment for orienting a plurality of LED modules of this invention under a microplate.

FIGS. 4 and 5 are schematic figures of a preferred orientation of one or more LED modules 10 with respect to a microplate 32. As indicated above, a single LED module 10 including a plurality of LEDs 12 emitting the same or different color light may be used to illuminate a microplate. LED module 10 may be oriented in any manner with respect to microplate 32 that allows a sufficient amount (an amount sufficient to allow the detector to detect light emitted by the samples held in wells of the microplate) of energy emitted by the LED's to reach the microplate. Some preferred LED orientations are shown in FIGS. 4 and 5 incorporate multiple LEDs 12 configured in linear modules 10. Each LED module 10 is mounted in an assembly referred to as a LED bank 34. LED modules 10 are configured with symmetry such that alignment pins, holes and screws in one LED module 10 will mate with those in another identical module 10 so that LED modules can be joined together to create an LED bank 34. Within a preferred LED bank 34, the LED modules 10 are parallel and both LED modules 10 face the same direction. This allows two or more LED modules 10 that include different wavelength LEDs to be conveniently mounted together and mounted to the instrument. Moreover, it is preferred that two LED banks 34 are oriented on opposite sides and only below a microplate 32 as shown in FIG. 4. LED banks 34 or LED modules 10 will typically be associated with a non-imaging optic, e.g., a reflective light pipe 36, to contain, direct, and diffuse the emitted light oriented towards a microplate.

FIGS. 5A and 5B, are schematics of LED modules 10 oriented in a manner that is intended to maximize the excitation of an area of the plate bottom. The illumination is angled at the bottom of the plate at approximately a 45° angle relative the long axis of the plate (along the row direction).

The instrument is designed to illuminate a maximum area. The illuminated width of this area depends on the external clearance to well bottom of the plate in question. In general, the instrument is designed to illuminate an area 80 mm wide and 111 mm long at the bottom of the plate. The illuminated width decreases as the illuminated surface of the plate is raised from the plate bottom. The illuminated width as a function of external clearance to well bottom (E) will be:

$$W = X - 2E \qquad \text{Eq. (1)}$$

where:
W=Illuminated width
E=external clearance to well bottom
X=illumination width at the microplate base, e.g., 80 mm The preferred LED module configuration discussed above may provide one or more of the following benefits: (1) It allows the user of the instrument to select either one of two colors for use in different assays without physical reconfiguration; (2) It allows easy interchange of modules for selection of additional colors with minimal effort; (3) It enables the use of two colors within a single experiment, which is useful for performing ratiometric assays; and (4) If higher excitation intensities are desired, two banks of the same wavelength can be joined as a module, doubling the number of available LEDs. Alternatively if even higher excitation intensity is desired both LED banks can be merged into one element that can contain even more LEDs, the extra LEDs filling the space otherwise used to connect the individual banks.

As discussed above, two LED banks 34 are preferably incorporated into the instrument, one on either side of the microplate to be illuminated. Each LED bank 34 may include one or more than one LED module 10. This orientation provides for substantial uniformity of illumination for all areas of the microplate. The LED modules 10 and or banks 34 are mounted a sufficient distance from the microplate to allow intermixing of the light from the individual LEDs. This contributes to the uniformity of illumination of the microplate and reduces the reliance on precisely matched LEDs. In fact appropriate mixing of the output of all the LEDs can make such a system robust to failure of any single (or more) LED. The loss of one LED leading to a fractional loss of intensity but no loss of uniformity. The intervening space between the LED module and the microplate is bounded by non-imaging optics, e.g., light pipes, 36 which may serve one or more of the following purposes: (1) To further diffuse the light from the LEDs, enhancing uniformity of excitation; (2) To direct the majority of the light toward the microplate which would otherwise be lost; (3) To confine the light from the LEDs and preclude its escape into the area around the instrument. This is particularly important for the case of UV excitation wavelengths, which pose a health hazard; and (4) To exclude emitted light from the region of the detectors and camera to reduce optical background.

The LED modules of this invention typically comprise a printed circuit board on which a plurality of LED's are arranged in a linear array though other arrangements may be equally suitable such as clusters and two dimensional patterns. The printed circuit board typically includes some to all of the LED power circuitry. The circuitry powering the LEDs may have one or more of the following characteristics:

a) Each individual LED may be turned off or on independently of the others;

b) Each individual LED may be adjusted for power level independently of others;

c) The LEDs may be grouped together arbitrarily for on/off and power level;

d) The LEDs may be turned on in with nanosecond accuracy; and e) The LEDs may be turned off with nanosecond accuracy.

These LED circuitry characteristics allow for the following modifications to the invention:

a) The LED module(s)/band(s) can be populated with more than one color (wavelength) in order to increase the flexibility of the system (allow assays requiring more than 2 colors, for example).

b) Ideally the light from the plurality of LED's is mixed in the light pipe so that all areas of the microplate are uniformly illuminated. This occurs in practice because the requirement for uniformity across a plate is not high. If, however, the LEDs are small enough or separated by wide gaps and/or the microplate is large enough, the LEDs may preferentially illuminate different areas of the microplate. In the present invention, the power levels to each LED can, if necessary, be varied to provide the most uniform illumination possible across the plate.

c) Since each LED may illuminate a different area of the microplate, the power levels to one or more LEDs can be varied to enhance illumination in various regions across the plate. This can be used to correct for nonuniformity in the collection efficiency of the lens/detector system, for example, to make this work the light source is on for a short period of time, shut off, and then the camera takes an image. The camera and the light source strobe at the same frequency but out of phase. Shifting the time delay adjusts the sensitivity to various lifetime fluorophores. Further description of MDC fluorescence lifetime techniques can be found in U.S. Pat. No. 6,317,207 the specification of which is incorporated herein by reference.

d) Arbitrary grouping of LEDs allows complex programming of varying levels of excitation power to be stored and applied rapidly.

e) The ability to precisely control the LED intensity by DC current control.

f) The ability to precisely and rapidly control the LED off/on state enables gating of the light reaching the detector—the light can be shut off before the image is transferred out of the CCD, thus eliminating the smearing of an image which otherwise occurs as the image is transferred off the active collection pixel area.

g) This gating also prevents the preferential exposure of certain areas (usually the central region) of the chip that results from use of a mechanical shutter.

h) This gating enables the performance of certain resonance effect analytical techniques (e.g., gated time-resolved fluorescence, fluorescence resonance energy transfer (FRET), and fluorescence lifetime) previously not feasible with this type of instrument, with appropriate additional gating of the camera. In practice, the LEDs are activated for a short period of time and then deactivated. After the LEDs have been deactivated, the camera is activated to take an image of the fluorescesing microplate.

II. Photodetectors

The LEDs of the LED modules and LED banks of this invention may be operated continuously or intermittently. It is preferred that LED's of the same or different wavelength in opposing LED arrays are operated (illuminate) simultaneously. Moreover, it is preferred that the LEDs are turned on and off much like a strobe light. Using the LED's like a strobe light can eliminate the need for a mechanical shutter between the LED's and the detector that detects the light emitted from each microwell. Activating the LEDs in a strobe-like manner also reduces LED heating thereby reducing the heat-induced LED intensity loss. Further, using the LEDs in a strobe-like manner may facilitate the ability of the heat sink to remove heat from the LEDs.

It is well known that LED's lose intensity as they heat up. Therefore, it may be useful to (1) monitor the LED intensity to determine if there is an intensity loss; and (2) to correct the detector readings to take any LED intensity loss into consideration. Towards this end, it is an optional embodiment of this invention to locate one or more photo detectors, such as photodiodes such that each photodiode preferentially receives excitation light emitted from one LED module. The photodiodes sense how much excitation light is emitted during a given pulse of the LEDs. The photodiodes may be filtered, but it is preferred that they are not because any fluorescence energy from the samples reaching the sensors is swamped (by many orders of magnitude) by the excitation light emanating from the LEDs. Each photodiode may be located within the light path of the system such as between the LED array and the sample or sample plate. Alternatively, each photodiode may be located remotely from the LED array and sample by using transfer optics such as mirrors to direct light to one or more photodiodes. Finally, photodiodes may be located in both of the locations mentioned above.

Sampling the actual emitted excitation light in real time enables monitoring of pulse-to-pulse variations in emitted light, which may be due to variations in:

1) Pulse length;
2) Temperature induced LED efficiency;
3) LED age; and
4) Current supplied to LEDs by drivers, or other factors.

The photodiodes will not account for the thermal shift sometimes seen in the LED spectrum. But since filters 20 selectively pass only wavelengths of interest, most of the significant power variation will be measured and can therefore be corrected for. The photodiode monitored levels may optionally be used to modulate the LED pulse times or intensities by turning off the LEDs once a certain level of photons had been acquired by the photodiode.

One or more photodiodes will typically be located between the LED modules and the microplate. The exact location of the photodiodes does not appear to be important. The photodiode readings can be combined and averaged or the readings can be used individually. The readings may be used to alter the LED power level to correct LED intensity, it may be used to calibrate or mathematically correct the detector readings or it may be used for a combination of these purposes.

III. Calibration and Data Correction Methods

LED's typically emit energy (light) over a fairly large range of wavelengths. This can cause problems in accurately detecting the amount of fluorescent light emitted from sample-containing wells of a microplate. In one aspect of this invention, the detected results can be used, as is, without correction. However, it is preferred that the detector is calibrated or that the detected results are corrected using one or more of the methods discussed below. Generally, correction for excitation-induced and other system errors is provided by simple algorithms. Known instrumental biases and artifacts that are correctable include:

1) Electronic (e.g., ADC) offset.
2) Detector dark signal
3) Non-spatially uniform background from emission-band light reaching the detector.
4) Time-dependent excitation energy fluctuations.
5) Non-spatially uniform excitation of the plate.
6) Non-uniform light collection efficiency of the lens.

A. Electronic Offset

In an ideal world, if no photons hit a pixel in the CCD, the camera would report a value of zero for this pixel. This is not the case. There is some noise associated with transferring charge and reading a pixel even if the charge in the well is nominally zero. In order to accommodate this noise the electronics are designed to offset the nominal zero value from the lowest measurable value. Typically this is done at the input to an analog to digital converter (ADC) and is thus referred to as an ADC offset. The offset is always present, and typically at a constant value, no matter the exposure conditions. The offset can be isolated and measured by operating the detector with no light input and no exposure time. Without correction the offset decreases the signal-to-background ratio.

In addition to the electronic offset of the detection electronics, photodetectors normally exhibit an electronic signal even in the absence of light. This dark signal is typically caused by thermal emission of electrons within the detector and is effectively reduced by cooling the detector. The dark signal is isolated by determining the electronic offset and then exposing the detector to no light for an extended period of time. The accumulated signal above the offset is the dark signal. The dark signal is proportional the exposure time. Alternatively the total signal of the detector measured at different exposure times in the dark can be used to determine the offset and dark signal simultaneously. The dark corresponds to the exposures varying part (slope) and the offset corresponds to the constant part (offset or intercept).

The instruments of this invention are capable of directly measuring ADC offset and apply correction to minimize the ADC offset error. The method for ADC offset correction is fairly straightforward. Several short exposures are taken with cooled camera (low dark signal), lights off, lens blocked, and, for cameras that have internal gain, gain off, and averaged together. Because these conditions minimize dark counts and exclude any other signal, this image effectively represents the offset. It is then subtracted from subsequent images prior to any other processing. The subtraction can be done on a pixel by pixel level (corresponding pixels of the ADC offset image are subtracted from the sample image), well by well level (corresponding wells of the masked ADC offset image are subtracted from those in the masked sample image) or as a constant (the average or maximum or minimum ADC offset value is subtracted from the sample image or masked sample image). The preferred method is to subtract the average ADC offset value from all pixels in the sample image. By measuring the offset in this way, residual offset is removed. If the camera is always operated in a low dark signal manner, e.g., chilled to −20° C. or below for most cameras or with very short exposures, no further correction for non-photon counts is required. If dark signal is significant then it must also be measured and removed. To remove dark signal an exposure factor must be calculated that represents the difference in exposure conditions between the measured dark image and the sample image. After removing ADC offset from both images the dark image, corrected for the exposure, can be subtracted from the sample image. As with the ADC offset correction, the full image or the masked images may be used.

B. Source Normalization

In the instruments of this invention, LEDs are preferably only pulsed on while the camera is actually recording data. This maximizes useful power output, minimizes heat buildup, prevents photobleaching of fluorescent samples (e.g., cells), and simplifies camera operation, e.g. prevents camera overexposure when the camera has no mechanical shutter. However, this method of pulsing the LEDs also induces temperature fluctuations and resultant efficiency and output fluctuations of the LED. This happens both within a single pulse and within a series of pulses. These effects can be minimized by measuring emitted light near the sample holder (microplate) with photodiodes as discussed above (integrating throughout the duration of each individual pulse) and monitoring the photodiode output. One photodiode may be used or multiple photodiodes may be used. In the case of multiple photodiodes their output signals should be combined, e.g., through averaging or weighted averaging. In a preferred embodiment two photodiodes are used and their signals are averaged. The photodiode signal for the first exposure of a series is recorded and used as a reference. Each subsequent image in the sequence is scaled (multiplied) by a factor based on the reference photodiode reading and the current photodiode reading. We refer to this process as Source Normalization.

C. Flat Fielding

Correction for the spatial variation of excitation energy across the plate was formerly done without regard to background. A uniformly fluorescent plate is illuminated and imaged. The averages of counts for each individual well are calculated. Dividing the maximum well value by each individual well value creates a table of correction factors. In subsequent experiments, each recorded well average is multiplied by the correction factor for that well prior to storage. The assumptions behind this calculation are:

1) The initial plate is in fact uniformly fluorescent.
2) The spatial variation in excitation is time invariant.
3) The counts in a given well represent only fluorescent signal which will faithfully represent the actual incoming excitation energy.

In practice this approach worked fairly well in prior instruments since the extremely narrowband laser created a low background that was relatively uniform, scaled with excitation intensity, and, most importantly, consisted only of the tiny fraction (10e−5) of excitation band light that passed through the emission filter.

Due to the broadband nature of the LED's spectrum, the LED modules generate significant amounts of energy within the emission band of dyes held in the microplate wells. Due to the angle-dependent efficacy of the excitation filter, some of this unwanted emission band energy reaches the microplate and ultimately the detector. This creates high background level reading and the distribution of this light is probably different from that of the excitation band light. Applying the prior art flat-fielding methodology to this situation introduces distortions into the data.

This becomes evident if one imagines the case of a uniformly fluorescent plate receiving spatially uniform energy in the excitation band of the dye, and also receiving non-spatially uniform energy in the emission band. The previous flat fielding routine would erroneously generate non-uniform correction factors and would thus distort subsequent images. In order to generate the correct table of flat-field correction factors, it is necessary to first remove the spurious counts due to emission band light from the LEDs. This is done in background subtraction, and must be done prior to both generating and applying the flat-fielding factors.

The new method of this invention is a Fluorescence Spatial Correction Factors Generation. The method includes: (1) taking a fluorescence image of a uniformly fluorescent plate. (This could be a single well microtiter plate (e.g. Nunc Omniplate) filled with fluorescein-based paint.); (2) Subtracting the ADC Offset from the image; (3) Reversing the plate and taking a second image; (4) Subtract the ADC Offset of the second image; (5) adding together the resultant 2 images; (6) dividing the result of step (5) by 2 and storing the result as a 2-image average; (7) defining the regions of the image comprising the individual wells of the assay plate and calculating the average pixel intensity for each well (masking); (8) identifying the highest intensity value well, and dividing this number by each of the other well intensity averages. The resulting matrix of values (one for each well) will represent the spatial correction factor for each well. The highest value well will have a correction factor of 1.0 and all the others will be higher; (9) storing this matrix as the Fluorescence Spatial Correction Factor XXX, where XXX is the wavelength of the excitation bank used and wherein each bank of LEDs will preferably have its own matrix; and (1) repeating Steps 2-9 for each excitation wavelength.

This flat-fielding procedure also corrects for the variation in lens collection efficiency over the field of view by following these steps:

1) Obtain a fluorescence image file.
2) Subtract ADC Offset.
3) Perform Background Subtraction.
4) Apply the mask definition to create the individual wells.
5) Multiply the well averages by the appropriate Fluorescence Spatial Correction Factor.

Figure 6:
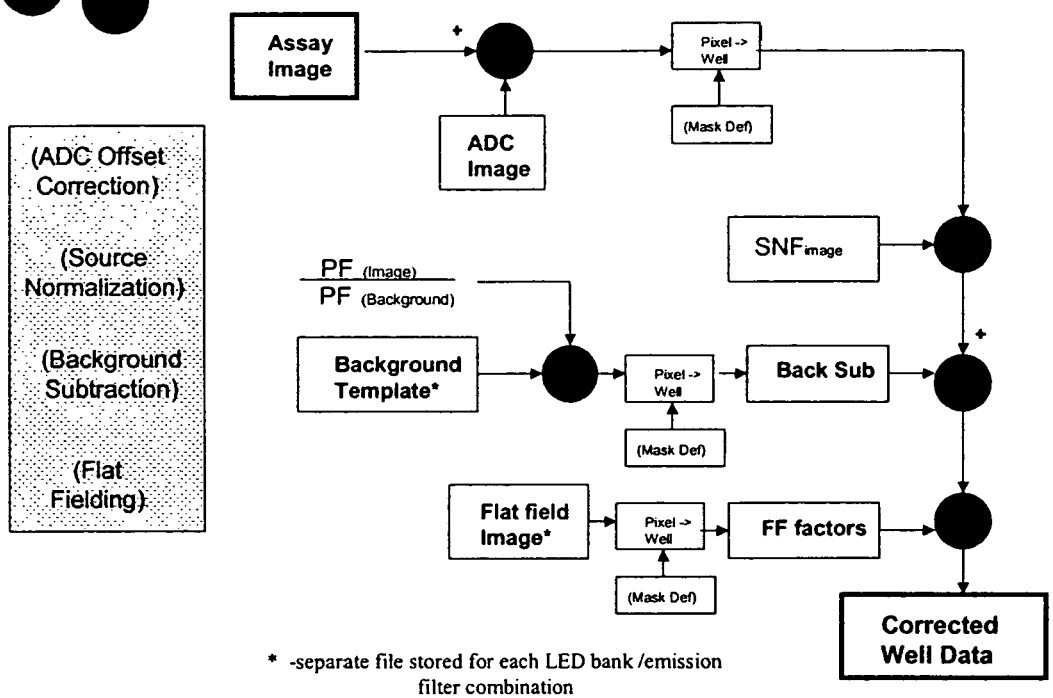
FIG. 6 is an assay data correction flow chart that identifies calibration method useful in conjunction with the present invention.
Figure 7:
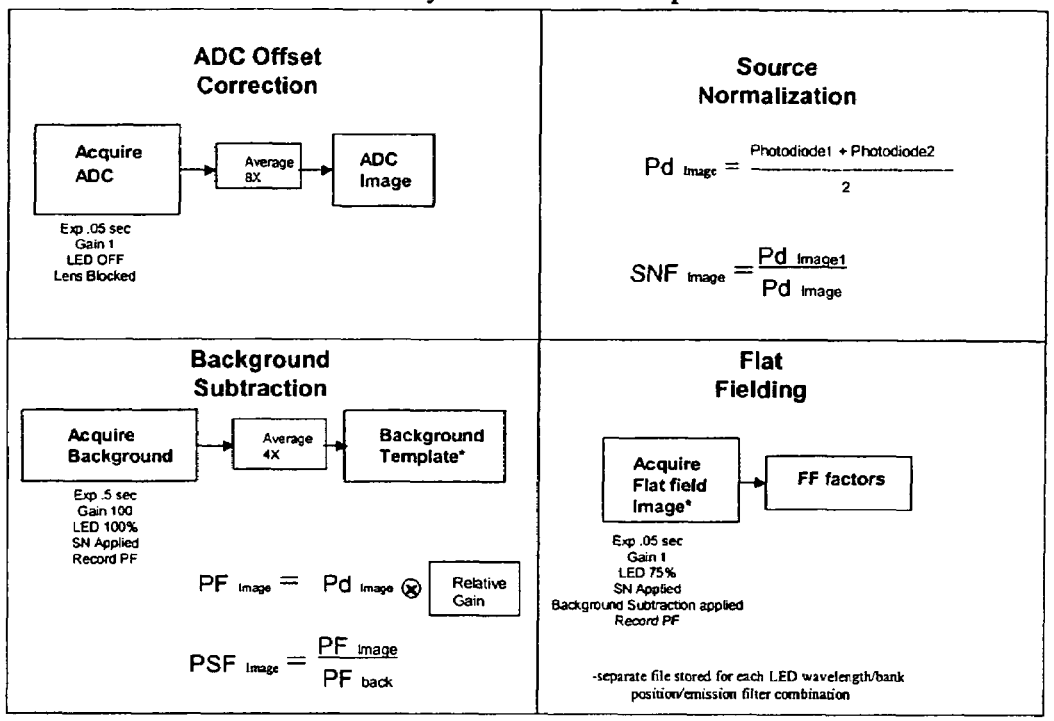
FIG. 7 is a representation of pre-assay calibration steps one or more of which may be used in conjunction with the present invention.

These steps are also set forth in the Data Correction flow charts of FIGS. 6-7.

D. Background Subtraction

In its simplest implementation, one would simply record an image of a nonfluorescent plate, using the same conditions (LED intensity, exposure time, camera gain) to be used in the actual assay. (The f-stop setting is assumed to be fixed in the system; otherwise it would also need to be included.) This image would capture the distribution of emission band light on the plate, and would be subtracted from each assay image prior to multiplication by the flat-fielding factors. In practice, however, this procedure is cumbersome, requiring measurement, storage and retrieval of images taken under all possible experimental conditions.

To avoid these difficulties, the Background Subtraction method of this invention uses a single image taken under known conditions. A Power Factor based on these conditions is stored with the image. This image is known as the background template. The Power Factor is defined as the product of the average of the two photodiodes and the Relative Gain.

The correspondence between the gain setting on the camera and the actual gain applied by the camera is not linear. Therefore, a curve relating the two must be generated. Prior to any other calibrations, a series of exposures is taken under identical exposure conditions, only varying the camera gain setting, and the actual gain applied is deduced by recording the output of the camera. These results are then stored in a table. The actual gain applied is referred to as the Relative Gain.

During an assay, the appropriate background template is retrieved, multiplied by the ratio of the two power factors (one from the stored template image, one from the current image), and the result is subtracted from the assay image. In another implementation, the power factors are calculated using the nominal LED intensity and exposure time. This method has the limitation that it is susceptible to error due to the deviation of the actual LED energy flux from the nominal (requested) flux.

This novel method of background subtraction will also be useful for removing background due to specular reflections of excitation energy off of the bottom of the microplate, which is sometimes observed.

The implementation of this correction scheme is summarized in the flow chart shown in FIG. 6.

E. Luminescent Assay Correction

Separate corrections may be made for luminescence-based assays.

Luminescence Spatial Correction Factor: Generation

Since there is no excitation source for luminescence assays, corrections are required only for Collection/Conversion Efficiency (lens and CCD factors) and ADC offset. The correction steps include:

1) Taking a luminescence image of a uniformly luminescent plate.
2) Subtract the ADC Offset from the image.
3) Reverse the plate and take a second image.
4) Again subtract the ADC Offset.
5) Add together the resultant 2 images.
6) Divide by 2 and store as 2-image luminescence average. This helps average out any imperfections in the uniformity of the plate. It also assumes that the plate is reasonably well-centered on the axis of the lens.

Luminescence Spatial Correction Factor-Application

The generated luminescence spatial correction factor is applied as follows:
1) Obtain a luminescence image file.
2) Subtract ADC Offset.
3) Apply the mask definition to create the individual wells.
4) Multiply the resultant image by the appropriate Luminescence Spatial Correction Factor and store.

The apparatus and methods of this invention are generally adapted to detect the occurrence of, or changes in, a luminescence signal from a sample such as a photoactive analyte due to excitation by the light source via the wavelength converter. The apparatus typically facilitates the detection of a change in sample luminescence, such as a change in the intensity, excitation and/or emission spectrum, polarization, and/or lifetime of the sample luminescence, or a combination thereof. The apparatus generally may be used in any suitable application, including high-throughput screening, genomics, SNPs analysis, pharmaceutical research and development, life sciences research, and/or other applications.

The detectable luminescence response may simply be detected, or it may be quantified. Where it is quantified, the intensity, wavelength, polarization, lifetime, and/or other spectral property of the luminescence response may be compared to a calibration standard. This standard may be the result of a calibration curve, a calculation of an expected response, or a luminescent reference material such as a luminescently labeled microparticle. The standard may be control samples present in selected wells of a multiwell microplate that also contains one or more samples.

The sample typically is a solution, cell, tissue, or other system containing one or more biomolecules that are biological in origin and/or that have been synthetically prepared. The sample optionally is or is derived from a biological sample that is prepared from a blood sample, urine sample, a swipe, a smear, or other physiological sampling method. Alternatively, the sample optionally is or is derived from an environmental sample, such as an air sample, a water sample, or a soil sample. The sample typically is aqueous, but may contain biologically compatible organic solvents, buffering agents, inorganic salts, or other components known in the art for assay solutions. Suitable samples (or compositions) include compounds, mixtures, surfaces, solutions, emulsions, suspensions, cell cultures, fermentation cultures, cells, suspended cells, adherent cells, tissues, secretions, and/or derivatives and/or extracts thereof. Depending on the assay, the term "sample" may refer to the contents of a single sample site (e.g., microplate well) or of two or more sample sites.

The detectable luminescence response may be used to determine the presence, absence, concentration, activity, and/or physical properties (including interactions) of a photoactive analyte in the sample. The apparatus may be used to detect a change in one or more samples, for example, due to a change in sample temperature and/or the addition of one or more reagents to the sample. In the latter case, the reagent may be a chemical reagent, or it may have a known or suspected biological activity or type of interaction with the sample. The apparatus also may be used to detect or quantify one or more aspects of biological activity in a sample.

The apparatuses and methods of this invention are especially suitable for simultaneously illuminating the bottom or top of a 96, 384, and even a 1536 well or lager sample plate and measuring the emitted fluorescence from all of the wells with a detector. The wells will typically contain cells loaded with fluorescent dye whose emission characteristics change upon binding with a particular ion (e.g., $Ca^{++}$, $H^+$ or $Na^+$). The cell plates have clear bottoms to allow for excitation and signal access and black walls to prevent signal diffraction.

The benefits of using a 1536 well format for decreasing reagent, compound and consumable costs while increasing throughput has been well documented for biochemical assays. The apparatuses and methods of this invention are especially useful for performing calcium mobilization and membrane potential assays in a 1536-well format.

The Apparatuses

The apparatuses of this invention are generally useful in light detection devices. Such light detection devices generally includes a light source (such as the LED light source of the present invention), a sample holder, and a detector.

The light source will be the LED light sources described above with reference to the present invention. The light source may be capable of use in one or more illumination modes.

The sample holder generally comprises any mechanism capable of supporting a sample and particularly a plurality of samples at a corresponding plurality of sample sites for analysis. Suitable sample holders include microplates, PCR plates, cell culture plates, biochips, hybridization chambers, chromatography plates, and microscope slides, among others, where microplate wells and biochip array sites may comprise assay sites. Preferred microplates are described in the following U.S. patent applications, each of which is hereby incorporated by this reference in its entirety for all purposes: application Ser. No. 08/840,553, filed Apr. 14, 1997; application Ser. No. 09/156,318, filed Sep. 18, 1998; and application Ser. No. 09/478,819, filed Jan. 5, 2000. These microplates (and/or cell culture plates) may include 6, 12, 24, 48, 96, 384, 864, 1536, 3456, 9600, and/or other numbers of wells. These microplates also may include wells having elevated bottoms, small (<50 µL) volumes, and/or frustoconical shapes capable of matching a sensed volume. A "standard" microplate includes 96 cylindrical sample wells disposed in a 8×12 rectangular array on 9 millimeter centers. Preferred PCR plates may include the same (or similar) footprints, well spacings, and/or well shapes as the preferred microplates, while possessing stiffness adequate for automated handling and thermal stability adequate for PCR. Preferred biochips are described in Bob Sinclair, Everything's Great When It Sits on a Chip: A Bright Future for DNA Arrays, 13 THE SCIENTIST, May 24, 1999, at 18. Preferred hybridization chambers are described in U.S. patent application Ser. No. 09/767,434, filed Jan. 22, 2001, which is hereby incorporated by reference in its entirety for all purposes.

The detector generally comprises any mechanism capable of detecting light transmitted from a sample and converting the detected light to a representative signal. Suitable detectors include charge-coupled devices (CCDs), intensified charge-coupled devices (ICCDs), charge injection device (CID) arrays, videcon tubes, photomultiplier tubes (PMTs), photomultiplier tube arrays, position sensitive photomultiplier tubes, photodiodes, and avalanche photodiodes, among others. The detector may be capable of use in one or more detection modes, including (a) imaging and point-reading modes, (b) discrete (e.g., photon-counting) and analog (e.g., current-integration) modes, and (c) steady-state and time-resolved modes, among others. The detector may be capable of automatically scaling the detection range and/or automatically selecting and switching between detection modes to improve detection accuracy, as described in U.S. patent application Ser. No. 09/643,221, filed Aug. 18, 2000, which is hereby incorporated by reference in its entirety for all purposes.

Other useful detectors include CCDs and ICCDs, the latter being especially suitable for the detection of low-intensity light generated using pulsed LEDs. The image-intensifier screen in front of the CCD chip in the ICCD may be activated selectively during desired time windows by supplying a voltage during the time windows. These windows may be of any suitable duration, including very short duration, e.g., a nanosecond or shorter, or of long duration, e.g., a minute or longer. Thus, the image intensifier may be used as a super-fast shutter capable of operating on nanosecond time scales, so that time-resolved fluorescence may be monitored over a very wide dynamic range of times. By supplying the voltage for a series of incrementally delayed time windows after excitation light pulses, the emission intensity as a function of delay time may be measured, thereby supplying a measure of the photoluminescence (e.g., fluorescence or phosphorescence) lifetime of the luminescence signals. The frequency domain equivalents also may be applied. In this case, the image intensifier gain and the illumination intensity are modulated at high frequency. The two signals heterodyne (homodyne) at the CCD (no high frequencies pass), and the phase and modulation can be determined. Further advantages and example usages of such time-resolved methods are described below.

Still other useful detectors include PMTs, in particular fast PMTs capable of monitoring emission over time scales between about 0.1 nanosecond and about 1 second. PMTs may be used singly or in arrays of two or more PMTs configured to detect light from a corresponding array of samples. PMTs may be especially useful in time-resolved assays, for example, to determine photoluminescence lifetime and/or time-resolved polarization, among others, using pulses of excitation light.

The apparatus also may optionally include an optical relay structure, such as a light pipe, configured to direct light from the light source to a sample holder and/or from the sample holder to the detector, a wavelength converter, a collimator, a compensator, and/or an emission spectral filter among others.

The optional optical relay structure may comprise any mechanism capable of directing light from a light source toward a sample (or examination site) and/or from a sample (or examination site) toward a detector. Suitable optical relay structures may include mirrors, lenses, and/or fiber optics, among others. Preferred optical relay structures include apochromatic elements, such as reflective optics elements including non-imaging optics, e.g., light pipes.

The optical relay structure may be selected to allow any of a variety of combinations of top and/or bottom illumination and/or detection of a sample holder, including the following specific combinations: (1) top illumination and top detection, or (2) top illumination and bottom detection, or (3) bottom illumination and top detection, or (4) bottom illumination and bottom detection. Same-side illumination and detection, (1) and (4), is referred to as "epi" and is preferred for photoluminescence and scattering assays. Opposite-side illumination and detection, (2) and (3), is referred to as "trans" and is preferred for absorbance assays.

Alternatively, or in addition, the optical relay structure may be selected such that illumination and/or detection occur at oblique angles. For example, illumination light may impinge on the bottom of a sample holder at an acute angle (e.g., about 45°) relative to detection. In comparison with a straight-on epi system (light source and detector directed at about 90° to sample holder) or a straight-through trans system (light source directed through sample holder directly at detector), an oblique system may reduce the amount of excitation light reaching the detector. An oblique system also may be used for unique kinds of illumination, such as total internal reflection.

Suitable optical relay structures for top/bottom and/or oblique illumination and/or detection are described in U.S. Pat. No. 5,355,215, issued Oct. 11, 1994; U.S. Pat. No. 6,097, 025, issued Aug. 1, 2000; U.S. patent application Ser. No. 09/337,623, filed Aug. 16, 1999; and U.S. Provisional Patent Application No. 60/267,639, filed Feb. 10, 2000, each of which is hereby incorporated by reference in its entirety for all purposes.

The optional emission spectral filter may comprise any mechanism capable of selecting the wavelength composition (or spectrum) of light admitted to the detector. Suitable emission spectral filters include interference filters, liquid crystal tunable filters, acousto-optic tunable filters, gratings, monochromators, and/or prisms, among others. One or more filters having suitable spectral characteristics (e.g., cutoff wavelength) may be housed in a filter selector such as a filter wheel or filter slider so that the wavelength composition of the emission light admitted to the detector may be changed by rotating or sliding or otherwise placing a preselected filter into the optical path. Any of the filters or filter selectors may be placed under computer control to automate filter passband selection in coordination with excitation wavelength selection.

Emission spectral filters may be used to transmit emission light and block excitation light in photoluminescence applications. Specifically, emission spectral filters with appropriate cutoff wavelengths can separate emitted or transmitted light from incident or illumination light due to differences in wavelength. For example, in conventional photoluminescence assays, the detected (emission) light is of longer wavelength than the corresponding illumination (excitation) light. In contrast, in multiphoton photoluminescence assays (and in anti-Stokes Raman scattering), the detected light is of shorter wavelength than the corresponding illumination light. In the absence of an emission filter, stray excitation light created, for example, by scattering and/or reflection may be detected and misidentified as photoluminescence, decreasing the signal-to-background ratio. Emission spectral filters for photoluminescence applications typically have wavelength cutoffs between about 200 and about 2000 nanometers.

An optional reference monitor generally comprises any mechanism capable of correcting for variations (e.g., fluctuations and/or inhomogeneities) in light produced by the light source and/or other optical elements. The reference monitor optionally may sample the intensity of the input beam (e.g., with each pulse) to provide a baseline for correcting measured photoluminescence levels (e.g., at different positions). For example, the reference monitor may be used to compensate for input beam variations due to pulse-to-pulse variations in output energy from the light source by reporting detected intensities as a ratio of the photoluminescence intensity measured by the detector to the excitation light intensity measured for the same time by the reference monitor. The reference monitor also may be used to perform additional functions, such as pausing device operation and/or alerting an operator if a light source fails or if light source intensities fall outside a preselected range.

Moreover, a selected well of a microplate containing a fluorescent material could be used as a reference for normalization of data with respect to light source intensity. Generally, the reference monitor may detect the diverted and sampled light using any detector capable of detecting the light and converting it to a signal suitable for use in correcting the sample signal(s).

The apparatus of this invention may include miscellaneous optical elements capable of performing additional and/or duplicative optical functions, such as "intensity filters" for reducing the intensity of light, "polarizers" for altering the polarization of light, and "confocal optics elements" for reducing out-of-focus light. Suitable miscellaneous optical elements and their implementation are described in U.S. Pat. No. 5,355,215, issued Oct. 11, 1994; U.S. Pat. No. 6,097,025, issued Aug. 1, 2000; U.S. patent application Ser. No. 09/337,623, filed Aug. 16, 1999; and U.S. Provisional Patent Application No. 60/267,639, filed Feb. 10, 2000, each of which is hereby incorporated by reference in its entirety for all purposes.

Other Aspects of this invention are disclosed below.

Arrayed LED Power Level Optimization

The instrument incorporates a special program for automatically selecting the optimum power levels for each individual LED in the array in order to achieve the most spatially uniform excitation possible. The program works as follows:

1) Put a uniformly fluorescent plate in the read position and take an image.
2) Divide the plate image into sectors. These may optimally be non-uniform in size and shape, but for starting purposes, use an evenly spaced 8×12 grid.
3) Turn on each individual LED sequentially (with equal intensity) & map its contribution to each sector of the image.
4) For each sector, rank the LEDs contributing light to that sector, highest to lowest.
5) Turn on all LEDs to half power and take an image. Calculate the intensity mean for each sector, and the mean, standard deviation and % CV for all the sectors.
6) Find the dimmest sector of the plate.
7) Find the LED that contributes most strongly to that sector.
8) Increase its power level 5%.
9) Take another image and re-calculate the stats for all the sectors.
10) See if the new CV is smaller than the old one.
11) If yes, go back to step 7, If no, reduce by 5%. Find the next biggest contributor or that sector.
12) Increase by 5%.
13) Re-calculate the stats for all the sectors.
14) See if the new SD is lower than the past one.
15) If yes, go back to step 13; otherwise reduce by 5%.
16) Repeat steps 6-16 five times.
17) Repeat steps 5-17 until no further improvement in SD is seen.

Once the optimal scaling factors for each LED have been determined, this information can be stored as a base configuration file. Any desired level of excitation is multiplied by these factors to determine the actual current sent to each LED.

Alternative Optimization by Row/Column

Since the we only have good control of light delivery in the row direction, it may be simpler and more effective to use a scheme that better reflects the physical constraints. A set of power factors will be created and used to calculate the absolute power level applied to each individual LED in given assay. Terminology as follows:

1) The Overall Power Factor (range 0.0 to 1.0) will apply to all LEDs and will determine the aggregate energy delivered in a given pulse. The Overall Power Factor is determined by the user for any given assay.
2) The Column Power Factor will be an array of 14 values (0.0 to 1.0), one value corresponding to each pair of LEDs as described below in step 2.
3) The Bank Power Factor will be an array of 2 values (range 0.0 to 1.0) that will apply to each of the 2 LED banks.
4) The Pulse Mode Power Factor is a single value (either 1.0 or 1.4) and is chosen depending on whether the LEDs will be pulsed or on continuously. For this purpose, anything over a 60% duty cycle will be considered continuous). Duty cycle to be calculated from assay settings by dividing exposure time by exposure interval.

In instrument use, each LED power level is determined by multiplying together the appropriate value for each of the 4 power factors.

The Column Power Factor is determined by the following procedure.

1) Divide the plate image into columnar segments (12 sectors of 2 columns each in a 384 well plate).
2) Logically group LEDs into pairs—one each from corresponding positions (mirror-image-wise) in the right and left bank. For example, begin with the two backmost LEDs in the right and left banks.
3) Sequentially activate the pairs and map their contributions to each columnar sector. There will probably be a strong correspondence between linear LED position and segment position.
4) For each sector, rank the LED pairs contributing light to that sector, highest to lowest.
5) Turn on all LEDs to half power and take an image. Calculate the intensity mean for each sector, and the mean, standard deviation and % CV for all the sectors.
6) Find the dimmest sector of the plate.
7) Find the LED pair that contributes most strongly to that sector.
8) Increase it's power level 10%.
9) Take another image and re-calculate the stats for all the sectors.
10) As long as the CV keeps decreasing and the power factor is less than 100%, increase the power level of that pair by 10% until that sector reaches the midpoint of the intensity rankings.
11) Go to the new dimmest sector and repeat steps 9 and 10 as long as the CV keeps decreasing.
12) Stop. Store the relative power levels for each LED pair, normalizing all values to 1.0 for the highest power level.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. An apparatus for measurement of a fluorescent emission from at least one sample, each sample being supported adjacent or embedded within a medium capable of contributing to background fluorescence, said apparatus comprising:

a) a light source operative to provide simultaneous illumination of a first wavelength selected to a plurality of samples to excite the fluorescent emission of light of a second wavelength by said plurality of samples wherein the light source is an LED array;

b) an optical sensor, responsive to light at said second wavelength; and c) wherein the light source is an LED module including:
i) a plurality of LEDs arranged in a linear array;
ii) a reflector surrounding each LED and having an opening; and iii) a tubular section adjacent to each reflector opening; and d) wherein the plurality of LEDs is mounted a sufficient distance from said plurality of samples to allow intermixing of the light from the plurality of LEDs.

2. The apparatus of claim 1, wherein the light source is at least one LED bank comprising at least two LED arrays, wherein the LED arrays are associated with each other such that the linear array of LEDs are parallel to each other and face in the same direction.

3. The apparatus of claim 1, wherein the light source is a pair of opposing LED banks oriented such that the energy emitted from the LEDs is angled at the bottom of the at least one sample at an oblique angle relative to an optical window of at least one sample holder.

4. The apparatus of claim 3 wherein the oblique angle is an angle of approximately 45°.

5. The apparatus of claim 1 further comprising a non-imaging optic located between the LED bank and the at least one sample.

6. The apparatus of claim 5, wherein the non-imaging optic is a reflective light pipe.

7. The apparatus of claim 1 further comprising at least one photodiode that optically samples the output of the LED array, wherein the at least one photodiode is optionally located at a position selected from: between the LED array and the at least one sample; remote from the LED array; or a combination of both locations.

8. An apparatus for the measurement of fluorescence emission from samples in the multiwell plate, comprising:
  a) a plurality of LED arrays operative to provide illumination to a plurality of samples in the multiwell plate, each LED array comprising at least two LEDs and a tubular section adjacent to each LED, each tubular section having an entrance end and an exit end, wherein the tubular sections are positioned such that LED light may enter the entrance end and exit the exit end;
  b) an optical detector, responsive to light emitted from the samples due to the illumination of the LED arrays; and
  c) at least two LED arrays which together are capable of simultaneously illuminating a plurality of samples in the multiwell plate; and
  d) a reflector adjacent each LED wherein each reflector is positioned to direct LED light into the entrance end of the adjacent tubular section;
  wherein the at least two LEDs is mounted a sufficient distance from the multiwell plate to allow intermixing of the light from the plurality of LEDs to the plurality of samples.

9. The apparatus of claim 8 wherein the tubular sections have an inner surface, at least a portion of which absorbs LED light.

10. The LED array of claim 9 wherein the inner surfaces of the tubular sections are black.

11. The LED array of claim 9 wherein the inner surfaces of the tubular section are rough.

12. The apparatus of claim 8 further comprising an optical filter positioned to intercept substantially all light that may exit from the exit end of at least one of the tubular sections.

13. The apparatus of claim 12 wherein the optical filter comprises an optical interference filter.

14. The apparatus of claim 8 wherein the LEDs in each LED array are arranged in a linear array.

15. The apparatus of claim 14 wherein the optic axes of the LEDs are parallel and wherein the LEDs face the substantially the same direction.

16. The apparatus of claim 8 wherein the optic axis of each LED array is oblique to the optic axis of the optical detector.

17. The apparatus of claim 16 wherein the angle between the optic axis of each LED array and the optic axis of the optical detector is approximately 45°.

18. The apparatus of claim 8 wherein the optic axes of the plurality of LED arrays form oblique angles with the optic axis of the optical detector.

19. The apparatus of claim 18 wherein the oblique angles are approximately 45°.

20. The apparatus of claim 8 further comprising a non-imaging optic to transmit the illumination from the exit of the tubular sections to the samples in the multiwell plate.

21. The apparatus of claim 20 wherein the non-imaging optic is a reflective light pipe.

22. A light detection device comprising:
  a) a plurality of light sources, each having a plurality of LEDs configured to produce light of a first spectrum;
  b) an optical filter configured to select light of a second spectrum within the range of the first spectrum;
  c) a system directing the light of the second spectrum from each light source to an examination area to simultaneously illuminate a plurality of samples; and
  d) a detector configured to receive luminescence light from one or more samples positioned in the examination area; and
  e) wherein the plurality of LEDs is mounted a sufficient distance from said plurality of samples to allow intermixing of the light from the plurality of LEDs.

23. The light detection device of claim 22, wherein at least one LED light source is pulsed.

24. The light detection device of claim 23, wherein the pulsed LED light source is triggered by the detector.

25. The light detection device of claim 22 further comprising a fluid delivery system that includes a dispensing device configured to deliver a fluid material to the sample.

26. The light detection device of claim 25, wherein the detector is configured to coordinate the reception of luminescence light from the sample with the delivery of the fluid material to the sample.

27. The light detection device of claim 25, wherein the luminescence light is used to determine a time-dependent property of the sample.

* * * * *